United States Patent [19]

Chuman et al.

[11] Patent Number: 5,063,058

[45] Date of Patent: Nov. 5, 1991

[54] **METHOD OF ATTRACTING *TRIBOLIUM CONFUSUM J.* USING 2,6-DIMETHYL-1-OCTANOL**

[75] Inventors: Tatsuji Chuman, Yokohama; Mikio Ono, Hamura, both of Japan

[73] Assignee: Japan Tobacco Inc., Tokyo, Japan

[21] Appl. No.: 512,424

[22] Filed: Apr. 23, 1990

[30] Foreign Application Priority Data

Apr. 25, 1989 [JP] Japan ................................. 1-105505

[51] Int. Cl.$^5$ ..................... A01N 25/10; A01N 25/08; A01N 25/34
[52] U.S. Cl. ..................................... 424/405; 424/78; 424/83; 424/408; 424/84
[58] Field of Search .................... 424/405, 84; 568/877

[56] References Cited

U.S. PATENT DOCUMENTS

| | | | |
|---|---|---|---|
| 4,284,622 | 8/1981 | Underhill et al. | 424/84 |
| 4,842,860 | 6/1989 | Sugiura | 424/84 |
| 4,923,119 | 5/1990 | Yamamoto et al. | 424/84 |

FOREIGN PATENT DOCUMENTS 0284363 9/1988 European Pat. Off. .
63-233942 7/1988 Japan .

OTHER PUBLICATIONS

Chemical Abstracts, published by the American Chemical Society, vol. 10, Mar. 27–Apr. 10, 1989, European Search Report.
T. Suzuki et al., *Agric. Biol. Chem.*, 44,2519 (1981).
K. Mori et al, Proc. Indian Acad. Sci. 100, 113 (1988).
Translation of Japan 63233942 above, uncertified, no authors.

*Primary Examiner*—Thurman K. Page
*Assistant Examiner*—E. Webman
*Attorney, Agent, or Firm*—Nixon & Vanderhye

[57] ABSTRACT

An attractant having attraction activity for to *Tribolium confusum J.*, which contains 2,6-dimethyl-1-octanol as a component exhibiting an attraction activity. 2,6-dimethyl-octanol can be diluted with an appropriated solvent, or carried by an appropriate solid-phase carrier in the form of tablets. The attactant can be effectively used in lure trapping.

7 Claims, No Drawings

METHOD OF ATTRACTING *TRIBOLIUM CONFUSUM J.* USING 2,6-DIMETHYL-1-OCTANOL

BACKGROUND OF THE INVENTION

1. Field of the Invention

The present invention relates to an attractant effective in relation to *Tribolium confusum J.*

2. Description of the Related Art

*Tribolium confusum J.* is a beetle generally known as a noxious insect parasitic on cereals. The beetle is parasitic not only on cereals such as flour, but also on secondary processed food (e.g., bread and cakes), and dried herbs, spices, zoological specimens, and the like. This beetle is therefore regarded as one of the most prominent indoor noxious insects, and there is a great demand for an effective method of preventing *Tribolium confusum J.* from living on, and removing it from, cereals, processed food, dried herbs, spices, and zoological specimens, and the like.

One of the methods which has been utilized to prevent noxious insects from living on, or removing them from, cereals is fumigation using compounds such as hydrogen phosphite, methyl bromide, DDVP, or the like. These compounds are harmful to humans, too. If they are applied indoors, they will be more harmful to humans than in an outdoor application. Hence, their use is limited to outdoor fumigation.

Recently, methods using the pheromones of specific insects, such as lure trapping, confusion and the like, are attracting much attention. These methods can be carried out simply by placing a dose of the attractant in a defined region, and are much easier than fumigation which is achieved by filling a limited space with a great amount of fumigate. In view of this, attraction methods are very useful in a workshop or a warehouse where many people are working. Many persons have been studying not only these methods but also the compounds to be used in these methods.

The inventors have found that 2,6-dimethyloctyl formate exhibits an attraction activity *Tribolium castaneum H.*, and described an attractant containing this substance, which is claimed in Japanese Published Unexamined Patent Application No. 63-233942.

However, no one has yet provided an attractant which exhibits attraction activity for *Tribolium confusum J.* and which can be manufactured economically. The pheromone of *Tribolium confusum J.* is identified with 4,8-dimethyl decanal (T. Suzuki, Agric. Biol. Che., 44, 2519 (1980)). The structure of this substance, i.e., 4,8-dimethyl decanal, is so unstable that the substance can hardly be used as an attractant.

SUMMARY OF THE INVENTION

Accordingly, it is an object of this invention to provide a stable attractant which exhibits attraction activity in relation to *Tribolium confusum J.* and is an economical attractant for lure trapping *Tribolium confusum J.*

The object can be attained by using as an attractant 2,6-dimethyl-1-octanol which exhibits *Tribolium confusum J.*

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENT

The inventors synthesized a number of compounds which have structures similar to that of the pheromone of *Tribolium confusum J.*, and tested them to see whether or not they have attraction activity to this particular kind of an insect. Of these compounds, 2,6-dimethyl-1-octanol was found to exhibit significant attraction activity for *Tribolium confusum J.*

Although 2,6-dimethyl-1-octanol is a compound generally known in the art (K. Mori et al., Proc. Indian Acad., (Chem. Sci.), 100, 113 (1988)), the present inventors were the first to make the discovery that this compound has attraction activity for *Tribolium confusum J.* This particular compound is chemically stable and, thus, exhibits its attraction activity for a long period of time.

This compound, i.e., 2,6-dimethyl-1-octanol, is represented by the following structural formula:

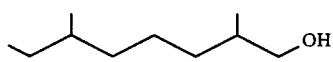

The compound can be identified with the following physical properties:

Boiling point: 117° to 110° C./26mmHg.

IR spectrum (cm$^{-1}$): 3350(s), 1040(s).

NMR spectrum (ppm, CCl$_4$): 0.7 to 1.0 (9H,m), 1.0 to 1.9 (10H,m), 3.11 (1H,s,OH), 3.26 (2H,d J=6Hz).

The attractant according to the invention, which is effective in relation to *Tribolium confusum J.*, can either be 2,6-dimethyl-1-octanol itself, or this compound may be used as a solution by dissolving it an appropriate solvent such as hexane, acetone, benzene, ether, methanol, or the like.

Alternatively, 2,6-dimethyl-1-octanol can be carried by a solid-phase carrier and used in the form of tablets. The carrier can be polypropylene, pulp, polysulfone nylon, nylon, polycarbonate, polyvinylidene chloride, polyvinyl chloride, polyvinylidene fluoride, polyurethane, cellulose ester, polyvinyl alcohol, epoxy resin, polyolefins, or the like. The weight ratio between 2,6-dimethyl-1-octanol and the solid carrier is 1:10 to 1:100,000, preferably 1:100 to 1:1,000. The tablets are made by stamping a plate of polypropylene, having a thickness of 3 mm, forming discs having a diameter of 10 mm, and injecting 1 ml of an ether solution of 2,6-dimethyl-1-octanol (1 wt%) into the discs by means of a syringe.

To lure trap *Tribolium confusum J.*, the attractant is placed an appropriate trap.

The attractant according to the, present invention has prominent attraction activity for *Tribolium confusum J.* Hence, if placed in a trap, the attractant attracts adult *Tribolium confusum J.* into the trap. Alternatively, it disturbs the ecosystem of adult *Tribolium confusum J.*, thereby preventing the insect from living on foods, dried herbs, spices, and zoological specimens, and the like, or driving the insect from these items. Moreover, the attractant according to the invention is chemically stable and, therefore, exhibits its attraction activity for a long period of time.

Also, the attractant according to the invention can be used to determine how and where *Tribolium confusum* J. generates, and how many individuals generate. In other words, the attractant helps to provide valuable data for use in deciding whether or not an insecticide should be used or when it should be applied, in order to kill *Tribolium confusum* J. or keep the insect away from foods, dried herbs, spices, and zoological specimens, and the like.

The present invention will now be described in greater detail, with reference to examples.

EXAMPLE 1

<A> Synthesis of 2,6-Dimethyl-1-Octanol (a) First, 31.4 g (0.2 mol) of 1-bromo-3-chloropropane and 14.2 g (0.1 mol) of cuprous bromide were added to 160 ml of dried THF. Then, these components were vigorously agitated by means of a stirrer, while being cooled to −10° C., thereby preparing a cooled solution. In the meantime, 4.8 g (0.2 mol) of metal magnesium and 27.4 g (0.2 mol) of 2-bromobutane were reacted in 160 mol of dried THF, thus preparing Grignard reagent. The Grignard reagent, thus obtained, was dripped into the cooled solution and reacted with it for about three hours, whereby 17.4 g of 1-chloro-4-methylhexane (1) was obtained at yield of 65%. This reaction is represented by the following formula:

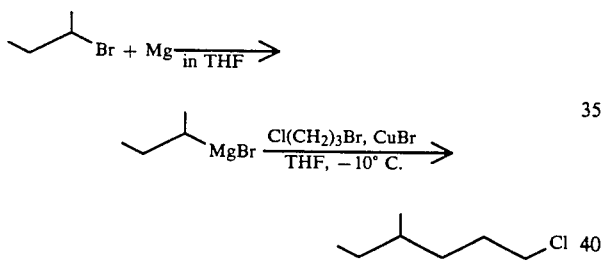

(b) First, 4 g (0.1 mol) of NaH as an oil was added to 100 mm of dried DMSO, forming a mixture. Into this mixture, 17.4 g (0.1 mol) of diethyl methylmalonate was dripped, while being stirred on an ice bath. Then, 13.4 g (0.1 mol) of 1-chloro-4-methylhexane was added to the resultant mixture and reacted with it at 70° C. for five hours. thereby obtaining 26 g of crude diethyl 4-methylhexylmethylmalonate (II). This reaction is described as follows:

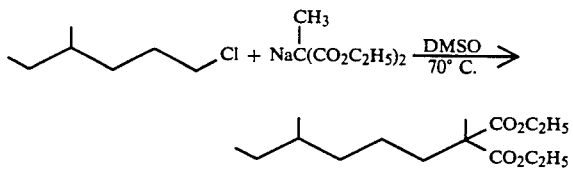

(c) First, 8.18 g (0.22 mol) of sodium hydroxide was dissolved in a mixture solution of 28 ml of water and 14 ml of methanol, thus forming a solution. Next, g of the crude product (II), not refined, was added to the resultant solution and reacted with the solution at 20° C. for three to five hours, thereby obtaining 18.4 g of 4-methylhexylmethylmalonic acid (III). This reaction is represented as follows:

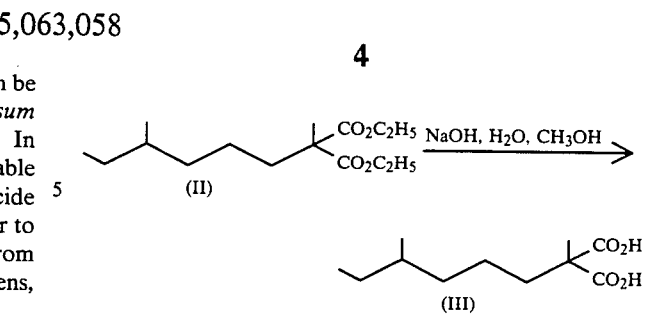

(d) 17 g of 4-methylhexylmalonic acid (III) was stirred on an oil bath, while being heated at 140 to 145° C. for 12 hours, and was thus subjected to decarboxylation. As a result of the decarboxylation, 12.5 g of 2,6-dimethyl octanoic acid at yield of 92%. This reaction is represented by the following formula:

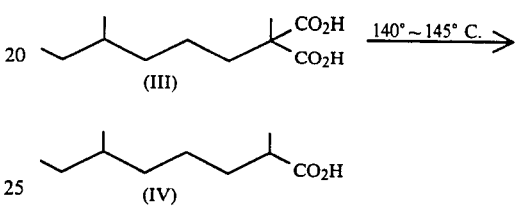

(e) First, 1.9 g (0.05 mol) of lithium aluminum hydride was suspended in 50 ml of dried ether while being cooled on an ice bath. Then, 8.6 g (0.05 mol) of 2,6-dimethyl octanoic acid was dripped into the resultant mixture, while the mixture was being stirred, and was reacted with the mixture for 20 hours, thereby obtaining 6.32 g of 2,6-dimethyl-1-octanol (V) at yield of 80%. This reaction is described as follows:

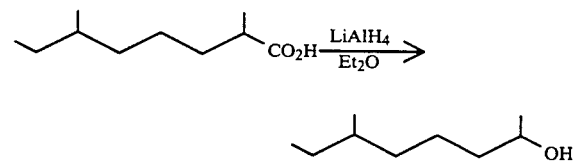

The boiling point of the product (V), thus obtained, was 52° to 53° C. at 0.7 mmHg. The IR- and NMR-spectrum of this product were identical to the data previously acquired.

<B> Attraction Activity of 2,6-Dimethyl-1-Octanol in Relation to *Tribolium confusum* J.

In order to evaluate the attraction activity which 2,6-dimethyl-1-octanol exhibits in relation to *Tribolium confusum* J., the following test was conducted.

Different amounts of 2,6-dimethyl-1-octanol were dissolved in acetone, thus preparing solutions having various contents of 2,6-dimethyl-1-octanol. Each solution thus obtained was applied to a circular sheet of filter paper having a diameter of 21 mm, and acetone was evaporated from both sheets of filter paper, thus making a test sheet. Acetone was applied to a circular sheet of filter paper having the same diameter, and acetone was evaporated from both sheets of filter paper, making a comparative sheet. A test sheet and a comparative sheet were placed in a plastic Schale having a diameter of 85 mm, set apart from each other by a distance of 30 mm. Thereafter, 30 adult *Tribolium confusum* J. were put in the Schale, and the Schale was closed with a cover. The Schale was placed in a room maintained at 28° C. and illuminated with red light. After 5 minutes, the Schale was opened, and the individuals of *Tribolium Confusum J.* attracted to the respective sheets of filter paper were counted.

The test described above was repeated six times for each test sheet, and the average number of the *Tribolium confusum J.* attracted to the test sheet, and that of the *Tribolium confusum J.* attracted to the comparative sheet, were obtained. The results are shown in Table 1:

TABLE 1

| Amount of Attractant Impregnated in Paper | Average Number of TCJ Attracted | |
|---|---|---|
| | Test Paper | Comparative Paper |
| 1 ng | 6.1 | 4.5 |
| 10 ng | 12.6 | 4.5 |
| 100 ng | 18.9 | 2.5 |
| 1 µg | 23.0 | 2.5 |
| 10 µg | 20.7 | 3.1 |

As can be understood from Table 1, 2,6-dimethyl-1-octanol has attraction activity in relation to *Tribolium confusum J.*

EXAMPLE 2

Various solutions were prepared by dissolving, in hexane, different amounts of 2,6-dimethyl-1-octanol prepared by synthesis <A> of Example 1. Each solution was applied by injection to a disc made of polypropylene, having a diameter of 1 cm and a thickness of 3 mm, and this disc was used as test disc. Also, as a control hexane only was applied to a., disc made of polypropylene and having the same diameter (1 cm), and this disc was used as a comparative disc. Further, two rectangular open boxes were made of a thick sheet of paper, measuring 6 cm×15 cm×2 cm. The inner surfaces of these boxes were coated with an adhesive. The test disc was placed on the bottom of the first box, thus making a test trap, and the comparative disc was placed on the bottom of the second box, thereby making a comparative trap. The test trap and the comparative trap, thus made, were placed on the floor of a closed test room, measuring 5 m×5 m×5 m, spaced apart from each other by 2 m. Then, 100 adult individuals of *Tribolium confusum J.* were released into the test room. The temperature within the test room was maintained at 28° C., and the room was illuminated with red light. Two days later, both the test trap and the comparative trap were removed from the room, and the *Tribolium confusum J.* individuals found in these boxes were counted.

The test described above was repeated six times, for each test disk. The results were as shown in the following Table 2:

TABLE 2

| Amount of Attractant Impregnated in Disc | Average Number of TCJ Attracted | |
|---|---|---|
| | Test Trap | Comparative Trap |
| 10 ng | 15.2 | 2.1 |
| 100 ng | 30.0 | 4.0 |
| 1 µg | 45.7 | 2.7 |
| 10 µg | 42.3 | 2.6 |
| 100 µg | 40.5 | 2.1 |

As Table 2 proves, 2,6-dimethyl-1-octanol has attraction activity in relation to *Tribolium confusum J.*

EXAMPLE 3

Two test traps identical to that used in Example 2, and also two comparative traps identical to that used in Example 2 were prepared. Two test rooms, both sized 5 m×5 m×5 m, were also built. A test trap and a comparative trap were put on the floor of both rooms, spaced apart from each other for 2 m. One hundred adult individuals of *Tribolium confusum J.* were released into the first test room, for lure trapping. One hundred adult individuals of *Tribolium castaneum H.* were put into the second test room, for lure trapping. The temperature in both test rooms was maintained at 28° C., and the interior thereof was illuminated with red light. Two days later, the *Tribolium confusum J.* individuals found in the test trap and comparative trap placed in the first test room were counted, and so were the *Tribolium castaneum H.* individuals present in the test trap and comparative trap placed in the second test room.

The lure trapping described above was repeated six times, for each type of insect. The results were as shown in the following Tables 3 and 4:

TABLE 3

(Lure Trapping of *Tribolium confusum J.*)

| Amount of Attractant Impregnated in Disc | Average Number of TCJ Attracted | |
|---|---|---|
| | Test Trap | Comparative Trap |
| 10 ng | 14.7 | 3.8 |
| 100 ng | 34.2 | 5.2 |
| 1 µg | 45.5 | 7.2 |
| 10 µg | 41.7 | 6.3 |
| 100 µg | 38.5 | 5.8 |

TABLE 4

(Lure Trapping of *Tribolium castaneum H.*)

| Amount of Attractant Impregnated in Disc | Average Number of TCH Attracted | |
|---|---|---|
| | Test Trap | Comparative Trap |
| 10 ng | 7.5 | 2.0 |
| 100 ng | 13.5 | 2.7 |
| 1 µg | 20.8 | 2.5 |
| 10 µg | 18.7 | 3.3 |
| 100 µg | 17.0 | 4.2 |

As is evident from Tables 3 and 4, 2,6-dimethyl-1-octanol has attraction activity in relation to *Tribolium confusum J.*

EXAMPLE 4

Two test traps were prepared which were identical to that used in Example 2, except that the solutions contained 2,6-dimethyl-1-octylformate instead of 2,6-dimethyl-1-octanol. Also, two comparative traps were prepared which were identical to that used in Example 2 and impregnated with hexane only. Using these test traps and these comparative traps, the lure trapping of *Tribolium confusum J.* and that *Tribolium castaneum H.* were carried out in the same way as in Example 3, for each solution having a different content of 2,6-dimethyl-1-octylformate. The results were as shown in the following tables 5 and 6:

TABLE 5

(Lure Trapping of *Tribolium confusum J.*)

| Amount of Attractant Impregnated in Disc | Average Number of TCJ Attracted | |
|---|---|---|
| | Test Trap | Comparative Trap |
| 10 ng | 5.7 | 2.3 |
| 100 ng | 4.5 | 3.3 |
| 1 µg | 3.2 | 2.3 |
| 10 µg | 4.0 | 3.5 |
| 100 µg | 3.5 | 2.0 |

TABLE 6

(Lure Trapping of *Tribolium casteneum H.*)

| Amount of Attractant Impregnated in Disc | Average Number of TCH Attracted | |
|---|---|---|
| | Test Trap | Comparative Trap |
| 10 ng | 14.7 | 1.3 |
| 100 ng | 29.8 | 2.0 |
| 1 μg | 42.0 | 1.8 |
| 10 μg | 34.8 | 2.5 |
| 100 μg | 32.0 | 2.3 |

As can be understood from Tables 5 and 6, 2,6-dimethyl-1-octylformate, which as been developed as attractant effective in relation to *Tribolium castaneum H.*, exhibited no particular attraction activity in relation to *Tribolium confusum J.*

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of attracting *Tribolium confusum J.* to a predetermined trapping location, which comprises placing an effective amount of 2,6-dimethyl-1-octanol at a predetermined trapping location, wherein said 2,6-dimethyl-1-octanol is supported by a solid carrier; wherein said solid carrier is in the form of a disc or a tablet; wherein said solid carrier is impregnated with said 2,6-dimethyl-1-octanol in an amount of 1/10 to 1/100,000 the weight of said solid carrier; and wherein said solid carrier is selected from the group consisting of pulp, polysulfone nylon, nylon, polycarbonate, polyvinylidene chloride, polyvinyl chloride, polyvinylidene fluoride, polyurethane, cellulose ester, polyvinyl alcohol, epoxy resin and polyolefin, thereby luring *Tribolium confusum J.* to the trapping location.

2. The method according to claim 1, wherein said solid carrier is in the form of a tablet.

3. The method according to claim 1, wherein said solid carrier is a disc having a thickness of 3 mm and a diameter of 10 mm.

4. The method according to claim 1 wherein the amount of 2,6-dimethyl-1-octanol impregnated in said disc is 1/100 to 1/1,000 the weight of said disc.

5. The method according to claim 3, wherein said disc is made of polypropylene.

6. The method according to claim 1, wherein said 2,6-dimethyl-1-octanol is used in the form of a solution dissolved in a solvent.

7. The method according to claim 6, wherein said solvent is selected from the group consisting of hexane, acetone, benzene, ether and methanol.

* * * * *